US011445926B2

(12) United States Patent
Van De Loo

(10) Patent No.: US 11,445,926 B2
(45) Date of Patent: Sep. 20, 2022

(54) DEVICE TO MEASURE AN EMBRYO'S HEART IN AN EGG

(71) Applicant: INNOVATEC, BESLOTEN VENNOOTSCHAP, Asperen (NL)

(72) Inventor: Philip Karel Marie-Louise Van De Loo, Vianen (NL)

(73) Assignee: INNOVATEC, BESLOTEN VENNOOTSCHAP, Asperen (NL)

(*) Notice: Subject to any disclaimer, the term of this patent is extended or adjusted under 35 U.S.C. 154(b) by 498 days.

(21) Appl. No.: 16/617,109

(22) PCT Filed: Jun. 7, 2018

(86) PCT No.: PCT/IB2018/054103
§ 371 (c)(1),
(2) Date: Nov. 26, 2019

(87) PCT Pub. No.: WO2018/225002
PCT Pub. Date: Dec. 13, 2018

(65) Prior Publication Data
US 2020/0138307 A1 May 7, 2020

(30) Foreign Application Priority Data
Jun. 9, 2017 (BE) .................................. 2017/5414

(51) Int. Cl.
*A61B 5/024* (2006.01)
*C12N 5/073* (2010.01)
(Continued)

(52) U.S. Cl.
CPC ........ *A61B 5/02416* (2013.01); *A01K 29/005* (2013.01); *A01K 41/065* (2013.01);
(Continued)

(58) Field of Classification Search
CPC ............ A61B 5/02416; A61B 2503/40; A61B 2562/02; A01K 29/005; A01K 41/065;
(Continued)

(56) References Cited

U.S. PATENT DOCUMENTS

2004/0107912 A1* 6/2004 Hebrank ............ G01N 21/3563
119/6.8
2009/0091743 A1 4/2009 Hebrank et al.
(Continued)

FOREIGN PATENT DOCUMENTS

EP 1543323 B1 5/2013
JP H09-127096 A 5/1997
(Continued)

OTHER PUBLICATIONS

International Search Report, dated Sep. 5, 2018, from corresponding PCT application No. PCT/IB2018/054103.
(Continued)

*Primary Examiner* — Michael P LaPage
(74) *Attorney, Agent, or Firm* — Nixon & Vanderhye

(57) ABSTRACT

Disclosed is a device for contactless measuring of an embryo's heart rate in an egg whereby infrared light is sent in the egg by one light source, and the reflection of that light is detected by one or more light sensors and converted into a signal representative for the heart rate, whereby a shield is provided to avoid light that is reflected on the egg shell interfering with the light sensors. The shield is provided at the light source and not at the light sensors, whereby a light tube is provided between the light source and the egg and the light tube is internally dimensioned and positioned such that a focused light spot is directed on the egg, and the light tube is dimensioned and positioned such that light reflected on the surface of the egg on the level of the light spot cannot directly reach the light sensors.

31 Claims, 3 Drawing Sheets

(51) Int. Cl.
*A01K 29/00* (2006.01)
*A01K 41/06* (2006.01)
*A01K 43/00* (2006.01)
*G01N 21/00* (2006.01)
*G01N 33/08* (2006.01)

(52) U.S. Cl.
CPC ............ *A01K 43/00* (2013.01); *C12N 5/0604* (2013.01); *G01N 21/00* (2013.01); *G01N 33/085* (2013.01); *A61B 2503/40* (2013.01); *A61B 2562/02* (2013.01)

(58) Field of Classification Search
CPC ...... A01K 43/00; C12N 5/0604; G01N 21/00; G01N 33/085
See application file for complete search history.

(56) References Cited

U.S. PATENT DOCUMENTS

| | | | |
|---|---|---|---|
| 2015/0138537 A1* | 5/2015 | Yamamoto | G01N 21/534 356/53 |
| 2016/0100557 A1 | 4/2016 | Adar et al. | |
| 2016/0299112 A1* | 10/2016 | Walukas | G01N 21/59 |
| 2017/0284989 A1* | 10/2017 | Hebrank | G01N 21/31 |
| 2018/0172657 A1* | 6/2018 | Suh | A01K 43/00 |

FOREIGN PATENT DOCUMENTS

| | | |
|---|---|---|
| WO | 02/086495 A2 | 10/2002 |
| WO | 2015/073939 A1 | 5/2015 |
| WO | 2015/145435 A1 | 10/2015 |

OTHER PUBLICATIONS

Belgium Search Report, dated Jan. 29, 2018, from corresponding Belgian application No. 201705414.

* cited by examiner

DEVICE TO MEASURE AN EMBRYO'S HEART IN AN EGG

BACKGROUND OF THE INVENTION

Field of the Invention

The present invention relates to a device to measure an embryo's heart rate in an egg.

Description of the Related Art

It is known to direct infrared light on an egg and to measure the intensity of the light that penetrated through the egg as a measure for the viability of an embryo in an egg.

It is also known that infrared light with a wavelength in the range of 700 nm to 1100 nm is the most suitable for this. The advantage of such infrared light is that it is less scattered when penetrating matter than light with a different wavelength. Such light is also well absorbed by blood.

Ascertaining whether an egg contains a viable embryo is done by determining a heart rate or movement of the embryo inside the egg. That can be measured by sending light through the egg. The light that has penetrated through the egg contains information as to whether the egg contains a viable embryo.

Because the heart pumps pulsed blood, the thickness of a blood vessel varies. The embryo's blood vessels will therefore vary over time as a result of a heart rate. This variation in thickness of the blood vessel, or the amount of blood that flows through, has an influence on the absorption of the light through the egg. A possible movement of the embryo also has an influence on the light path and thus the light intensity that goes through the egg.

Blood absorbs light; the thicker a blood vessel, the more light is absorbed by the blood. This means the variation of the thickness of a blood vessel as a result of an embryo's heart rate can be measured. Thus, there is a direct relationship between absorption of the light and the thickness of the blood vessel. This technique has been applied for years in the medical sector.

It is clear that several difficulties occur when measuring an embryo's heart rate in an egg.

Existing systems, as described below, have a number of disadvantages.

JPH09127096 describes a central emitter and 4 receivers which are placed on an egg to measure the life or death of an egg. The 4 receivers receive the light of the emitter that is reflected by the egg. The detected signal is processed.

EP1381859 describes a similar system whereby infrared light is directed on an egg and light that passes through the egg is detected.

EP1543323B1 describes a method to determine the viability of an egg in which infrared light is directed on an egg from a plurality of directions and a part of the received infrared light is converted into a signal that is processed to verify whether there is a cyclical variation in the signal. An embodiment is described in which 4 infrared emitters and 1 receiver per egg are used.

A major disadvantage of these systems is that the measuring equipment needs to be put or pressed onto the egg. Relating to hygiene of the handling of an egg this is highly undesirable.

Another important disadvantage of the aforementioned systems is the slow measurement speed. In poultry hatcheries a high measurement speed is very important because the market demands a high machine line capacity at the lowest possible machine investments.

Another disadvantage of existing systems is that the electronics are very sensitive to changes. When the embryo in the egg moves, it is many times greater than the signal of a blood vessel that varies in thickness as a result of the heart rate. Consequently, the electronics can quickly go into overdrive and time is lost to repair it.

Yet another major disadvantage is the influence of the scattered light on neighbouring eggs. Neighbouring eggs thus receive light that is not from the own light source and has not even passed through or reflected on the egg.

Light from the own light source that is reflected on the egg shell also interferes with the receivers which go into overdrive because of this. The exit of the light sensor will clip against the limit and measuring the heart rate is no longer possible then.

To solve that problem, "shielding means" are used on the level of the receivers. This method is disadvantageous, as this means part of the informative signal is shielded and will not be received. This signal is already very weak. Moreover, these shielding means come into contact with the egg, which is really not desirable.

US 2016/100557, WO 2015/145435, US2009/091743 and WO 2015/073939 describe similar systems.

The purpose of the present invention is to provide a solution to at least one of the aforementioned and other disadvantages.

SUMMARY OF THE INVENTION

To this end, the invention relates to a device for contactless measuring of an embryo's heart rate in an egg whereby infrared light is sent in the egg by one light source, and the reflection of that light is detected by one or more light sensors and converted into a signal representative for the heart rate, whereby shielding means is provided to avoid light that is reflected on the egg shell interfering with the light sensors, characterised in that the shielding means is provided at the light source and not at the light sensors, whereby a light tube is provided between the light source and the egg and the light tube is internally dimensioned and positioned such that a focused light spot is directed on the egg, and the light tube is dimensioned and positioned such that light reflected on the surface of the egg on the level of the light spot cannot directly reach the light sensors.

The light tube has a double function: as shielding means and as focusing means. This double function is accomplished by its positioning and (internal and external) dimensions.

On one end the light tube is positioned around the light source so no light can escape. The internal dimensions of the light tube are such that a very focused spot of light is directed on the egg. On the other end the light tube comes very close to the egg without making contact with the egg. In this way maximum light is directed on the egg and minimum light is scattered from the surface of the egg towards the light sensors. It is important that the sensors, which are very sensitive, are protected from scattering light that does not contribute to a meaningful heart rate signal.

As such the light tube also acts as a shielding means. Furthermore, the external dimensions of the widened edge at the end of the egg disables scattered light on the surface of the egg to directly reach the light sensors.

This setup allows space saving since each egg has its own light source, light tube and light sensors. Furthermore the shielding means is provided at the light source and not at the light sensors. The already very sensitive light sensors must detect as much light as possible, and this detected light must be meaningful in the sense that the light must have traveled through/in the egg and represent the heart rate of the embryo. Scattered light on the surface of the egg is meaningless light.

An embryo's heart rate is measured by, on the one hand the reflection of the light on a blood vessel which can vary with the variation of the blood vessel as a result of the heart rate, and on the other hand the absorption of the light that went through the blood vessel.

In the end it is about the light that went through the egg. This may contain information about a heart rate in the egg.

In a preferred embodiment of a device according to the invention that the half exit angle of the light source is 3° to 4°.

Preferably, the infrared light source emits light with a wavelength in the range between 700 nm and 1100 nm.

Preferably, the light source has the smallest possible exit angle such that the smallest possible light spot falls on the surface of the egg.

Optionally, a lens can be used to focus the light more or a laser beam, but they are both more expensive options.

Preferably, the light source is an infrared LED which is widely available and affordable, or a laser beam.

The device of the invention is limited to one light source per egg position. Using only one light source has the advantage that only one strong focussed light is directed towards the egg and limits light diffusion and light scattering, which in turn makes detection of reflected light stronger and less sensitive.

Preferably, the device contains several light sensors or infrared receivers. In a specific embodiment the light sensors are located around the light source in one and the same plane. In another embodiment the light sensors are located in another position, e.g. in a curved surface partly around the egg.

The advantages of the use of several sensors is that more light is received, and from several directions. The noise in the received signal is suppressed many times better following the averaging of the noise, which improves the signal-noise ratio. The mutual tolerances in the light sensors are also averaged.

The light sensors or receivers to detect the light received have to be very sensitive. The part of the light that contains information regarding the heart rate and which reaches one of the light sensors, is therefore very weak. Indeed, a big part of the light that is sent to the egg is lost due to reflection, scattering and absorption and never reaches a blood vessel.

The light sensor can be a "standard" light sensor based on silicon, such as e.g. the TSL250 series.

The light sensor is sensitive to the wavelength of the emitted IR light of the light source. The wavelength of the infrared light lies in the range between 700 nm and 1100 nm, preferably 850 nm.

In a special preferred embodiment of a device according to the invention a light tube is provided between the light source and the egg, whereby the light tube is dimensioned and positioned such that a very focused light spot is directed on the egg.

The light of the light source is more focused and is directed on the egg in a small beam.

In a specific embodiment of a device according to the invention the light tube on one end is provided around the light source.

In a specific embodiment of a device according to the invention the light tube is dimensioned such that light reflected on the surface of the egg on the level of the light spot cannot directly reach the light sensors.

In a more specific embodiment of a device according to the invention the light tube is provided with a broadened edge on the side of the egg, whereby the broadened edge is dimensioned and positioned such that light reflected on the surface of the egg on the level of the light spot cannot directly reach the light sensors. The sensors need to be located in the shadow field of this edge.

In a specific embodiment of a device according to the invention the light tube is provided with a widened edge at least at the end near the egg, whereby the broadened edge is dimensioned and positioned such that light from the light spot reflected on the surface of the egg cannot directly reach the light sensors.

In another preferred embodiment of a device according to the invention the light tube is dimensioned and positioned in relation to the light source such that all the light of the light source is sent through the light tube in the direction of the egg.

Preferably, the light tube is made such that all light of the light source falls in the light tube. In this way an intense focused light spot is directed on the egg via a fine beam of light.

The light tube is located between the light source and the egg. The light source can be wholly or partly contained in the light tube.

The light tube does not make contact with the egg.

The length of the light tube is such that the light is directed on the egg in a fine beam. Preferably, the light tube is cylindrical both on the inside and the outside.

The light tube can be provided with means that bundles the light in a fine beam.

In another preferred embodiment of a device according to the invention, another shielding means can be provided to ensure there is no contact between the light source and the egg, on the level of the light spot, to prevent the light reflecting directly on the light sensors.

A big part of the light that is sent in an egg is reflected directly by the surface of the egg. It is important that light that is directly reflected on the surface of the egg cannot reach the light sensor directly. The informative signal would be lost because of this. Indeed, the light that is sent in the egg and contains the heart rate information of an embryo in the egg, is so much less intense than this directly reflected light on the surface of an egg. Without shielding means this strongly reflected light can directly reach the sensor and make it go into overdrive.

Existing systems will protect the light sensor/receiver itself against light that is reflected on the surface. However, consequently a part of the informative reflected light of the blood vessels is blocked which means it cannot be detected. This is very disadvantageous for a sensitive and correct heart rate measurement.

Yet another way to minimise light that is reflected on the surface of the egg is by using a light source and light tube with a very narrow angle. In this way the light spot on the egg will be very focused and consequently minimise reflection and scattering on the surface.

Certain existing systems will use several light sources to measure the heart rate. In view of the even greater scattering of light on the surface of the egg that is very disadvantageous.

In another special preferred embodiment of a device according to the invention there is no contact whatsoever with the egg, except to support the egg.

The measurement of the heart rate is contactless. That implies there is no contact at all between the egg, and the light source, nor the one or more light sensors, nor any other material. The egg only makes contact with the incubation tray, tray or another support of the egg.

Contactless measuring is very important in the egg industry due to the danger of contamination.

Contactless measuring requires a very special measurement setup and measurement method. The use of only one focused light source is important in this.

In a preferred embodiment of a device according to the invention the device comprises means which keep the luminous intensity of the light source stable.

In another preferred embodiment of a device according to the invention the device comprises means to suppress mechanical vibrations on the light source, the light sensors and the egg.

During the measurement, vibrations need to be avoided. The system may not be exposed to vibrations of machines that are necessary to handle the eggs, such as conveyor belts. Indeed, they can produce frequencies in the same order as an embryo's heart rate in the egg.

The device is preferably also provided with an infrared filter between the light source/light tube and the egg. This filter only allows light through of a certain wavelength. Consequently, one has an extra assurance that the non-infrared part of light, coming from other light sources, does not fall on the light sensor.

The measuring of an embryo's heart rate in the egg is done in a way that allows contactless measuring. The measurement method also prevents the eggs from warming up during the measurement by directing an infrared light on the egg for too long a time. The measurement also excludes interference of the heart rate of embryos in neighbouring eggs.

In a preferred embodiment of a device according to the invention the device has measurement means, whereby a tray is provided to hold a matrix of eggs and above the eggs a sensor array is provided per egg comprising a light source, light tube and light sensors, characterised in that at least during the measurement, a mechanical shortcut is provided between the tray and the sensor array, or between the tray and the measurement means, so as to eliminate vibrations or to vibrate with the same frequency.

In a preferred embodiment according to the invention, the mechanical shortcut comprises un upward and/or downward pressure force.

In a preferred embodiment of a device according to the invention, the device is provided with a matrix of eggs which are each provided with their own light source, light tube and one or more light sensors.

In a specific embodiment of a device according to the invention, every egg is sampled several times to measure an embryo's heart rate in the egg. The signal that is representative for an embryo's heart rate in the egg consists of, or is formed by means of, two or several of these samples.

Every egg is sampled or measured several times. Sampling occurs with an interval. Other eggs are sampled in that interval.

"Sampling" or "measuring" means that the light source sends the IR light in the egg and the light sensors do or don't receive a signal of light reflected from in the egg.

Sampling is done by briefly simultaneously switching on and off the light source and light sensors in question of the egg to be measured.

In a special embodiment of a device according to the invention, measuring is not continuous.

Per egg a signal is formed with the multiple samples of the egg in question, whereby the variation of the signal shows the viability of an egg.

To filter the heart rate out of the signal in the end the necessary algorithms have been implemented in the hardware and software.

Not all eggs are sampled at the same time, only certain eggs selected by a scan/sample sequence. This sample sequence is determined according to a specific algorithm.

Only those eggs at a sufficient distance barrier from each other are sampled at the same time. Neighbouring eggs are not sampled at the same time.

The device is provided with a matrix of light sources and light sensors. According to this matrix the eggs to be measured are in a tray under their light source in question.

The device is provided with means to determine the sample sequence to minimise the number of scans/samples necessary to sample all eggs.

The device can be used to measure an embryo's heart rate in an egg of any incubation period.

Both the heart rate and the embryo's movement are measured. Movement results in a greater variation in light intensity than a heart rate, but the embryo does not always move. If the embryo is not moving, it does not mean it is not viable. However, the movement does have to be measured because the heart rate measurement would be lost in the strong signal caused by movement of the embryo.

The measured signal is very weak. That is because only a very small part of the light passes a blood vessel or reflects on the blood vessel in the end. Of that part of the light only a much smaller part reaches the light sensor in the end.

The light is hugely scattered on the way and absorbed when passing all kinds of different layers of the egg. In particular the egg shell diffuses the light as well as the present meat of the embryo. The liquid in the egg and the meat absorb a big part of the (infrared) light.

The light signal that contains information relating to an embryo's heart rate in the egg and which in the end manages to reach the light sensor, is many times weaker than the light which via reflections chiefly on the surface of the egg manages to reach the light sensor. That can increase to a factor over 10,000.

In contrast, a reasonable part of the surface of the egg emits light that may contain information regarding the embryo's heart rate in that egg. Each point on the surface can be seen as a separate light signal. Part of each of these light signals can reach the light sensor.

With the help of a light sensor, the light received is converted into a voltage.

The largest part of the light received by the light sensor is the result of the reflection. Only a small part of the light contains information about the heart rate. The reflected part can be seen as an offset.

It is important that during the heart rate measurement the luminous intensity of the light source remains constant and the power supply for the light sensor remains as constant as possible. The necessary measures have been taken for this.

Furthermore, the distance between light source-egg-light sensor preferably remains constant during the measurement and the egg is not moving. Preferably, the whole set-up is vibration free such that there are no external mechanical vibrations.

In a preferred embodiment of a method of the invention, during the measurement the light source and light sensors, and the eggs are positioned vibrationless.

Even more preferably, external fluctuating light beams that can fall on the light sensor are avoided.

Interference or crosstalk of neighbouring eggs must be avoided. Indeed, an embryo's heart rate of a neighbouring egg can be measured because the sensor has to be so sensitive.

The system must be able to detect very low frequencies, from 0.5 Hz to 7 Hz for a heart rate from 30 to 420 beats per minute.

The invention also relates to a method for measuring an embryo's heart rate in an egg.

In a preferred embodiment of a method according to the invention to measure an embryo's heart rate in an egg, whereby infrared light is sent by a light source in the egg, and the light is reflected by the blood vessel or on the edge of the blood vessel and is detected by one or more light sensors and converted into a signal representative for the heart rate, a very focused light spot is directed on the egg.

In another preferred embodiment of a method according to the invention to measure an embryo's heart rate in an egg, based on a device as described above provided with an infrared light source and one or more light sensors per egg, the method comprises the following steps:
 a) Determining a sample sequence for the simultaneous measuring of non-neighbouring eggs,
 b) Simultaneously sampling of the eggs per sequence, and subsequently repeating for the eggs of another sequence,
 c) Repeating step b for n times,
 d) Processing the n signals per egg into a signal representative for the heart rate of a living embryo in the egg.

When the multiple samples are placed after each other, a varying signal is created if a heart rate is measured.

In a specific embodiment of a method according to the invention, in step a) sample sequence 1 comprises the selected non-neighbouring eggs in the matrix of FIG. 5-1, sample sequence 2 comprises the selected non-neighbouring eggs in the matrix of FIG. 5-2, sample sequence 3 comprises the selected non-neighbouring eggs in the matrix of FIG. 5-3 are scanned, and sample sequence 4 comprises the selected non-neighbouring eggs in the matrix of FIG. 5-4, and in step b) the selected eggs of sample sequence 1, 2, 3 and 4 are scanned in a consecutive time slot.

In a specific embodiment of a method according to the invention the light source and light sensors of the selected eggs are synchronously switched on and off per measurement of the eggs in step b). This synchronous switching on and off is done with a very short measuring time.

In an even more specific embodiment of a method according to the invention no contact is made between the measuring equipment and the egg.

During the measurement the light source, the light sensors and the eggs are positioned in a vibration free way.

In a certain embodiment, a light sensor is also placed under the egg in the support plate. This light sensor is also switched simultaneously with the sample sequence of the egg in question. This makes it possible to determine how much light also passed through the egg. This measurement is therefore not a heart rate measurement but an intensity measurement.

That process is also called candling, and is generally used in the hatchery industry. The eggs that let through a certain higher level of light, are often collected separately because these eggs still have an economic value. They are not viable eggs but are not waste either. The eggs where little light goes through, less than the set value, and do not have a heart rate, are usually removed from the process as waste. These dark, non-viable eggs often constitute a danger for the hygiene in a hatchery because they may be gas eggs or exploders. These are eggs in which bacteria grow that are potentially dangerous for the hygiene, and therefore are removed from the process. These measurements also provide important data about the quality of the eggs, data with which a hatchery can be managed.

A major advantage that only 1 light source is positioned straight above the egg, is that the light of this one light source goes through the egg much better, than if there were several light sources around the egg.

BRIEF DESCRIPTION OF THE DRAWINGS

With the intention of better showing the characteristics of the invention, a preferred embodiment of a device to measure an embryo's heart rate in an egg according to the invention is described hereinafter, by way of an example without any limiting nature, with reference to the accompanying drawings wherein.

DESCRIPTION OF THE PREFERRED EMBODIMENTS

Figure 1:
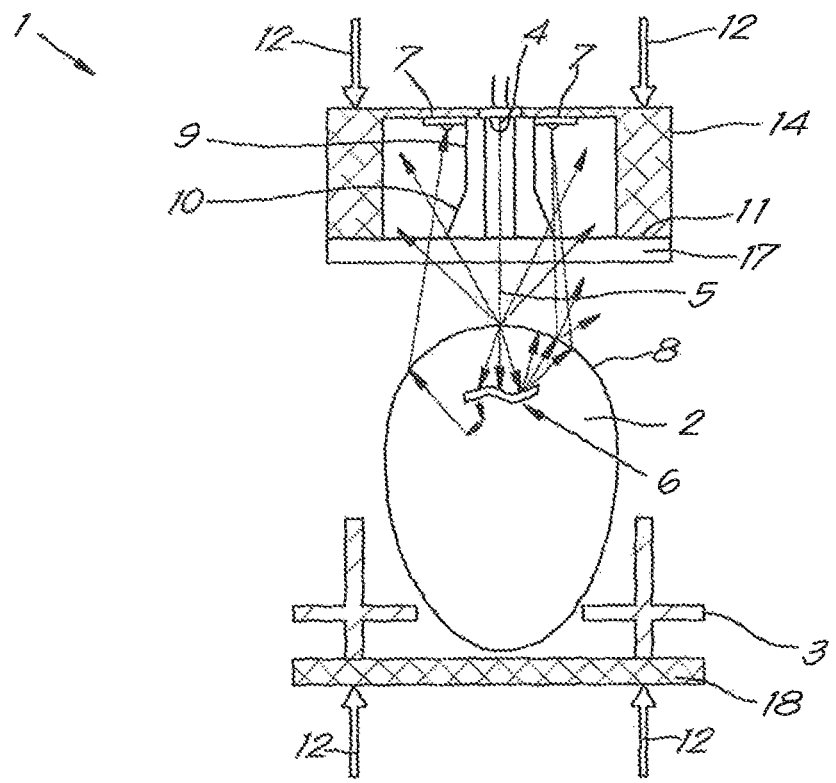
FIG. 1 schematically shows a preferred embodiment of a device according to the invention whereby the measurement of an embryo's heart rate in one egg is presented.

FIG. 1 shows a preferred embodiment of a device 1 to measure an embryo's heart rate in an egg 2.

The egg 2 is held on one of its ends or placed in an incubation tray, tray or other support 3. The light source 4, which is centrally positioned above the egg 2, sends infrared light 5 of approximately 850 nm in the other end of the egg 2.

The IR light 5 (see fine arrows) enters the egg 2 and is reflected on a blood vessel 6. Part of this reflected light 5 is detected by one or more light sensors 7.

IR light 5 is also reflected on the surface 8 of the egg 2. To prevent the reflected light 5 from falling directly into a light sensor 7, a light tube 9 is provided around the light source 4. The light tube 9 is provided between the light source 4 and the egg 2. On the side of the egg, the light tube 9 is provided with a broadened edge 10 dimensioned and positioned such that the light directly emitted by the light source 4 and directly reflected on the egg surface 8 is not reflected on the light sensor 7.

Several light sensors 7 are positioned next to the light source 4 in one and the same plane. The more light sensors 7 the better the light is detected that passed through a blood vessel 6 or is reflected on the edge of a blood vessel 6. In certain embodiments three or six light sensors 7 are used.

The light sensors 7 are positioned around the light source 4 and the light tube 9, such that IR light 5 reflected on a blood vessel 6 in the egg 2, can reach one or more light sensors 7. And such that the broadened edge 10 of the light tube 9 prevents IR light 5, directly reflected by the light source 4 on the surface 8 of the egg 2, from reaching a light sensor 7.

On the end of the light tube 9, an infrared filter 11 is optionally provided. In this way IR light with a wavelength >700 nm, for example, can pass through the filter. The filter can be modified so that, for example, only IR light of 850 nm passes through the filter 11.

Preferably, the glass plate 17 has a low infrared absorption. The glass plate 17 can also be provided with a lens to only capture the light from the own light source 4 and not of a neighbouring egg. The glass plate 17 also has a hygienic function such that the glass plate can be easily cleaned.

The part of the device 1 that is located above the glass plate 17 is contained in a casing or sensor array 14. This contains the light source 4, the light tube 9 and the light sensors 7. Preferably, the sensor array 14 is made of infrared light absorbing material such as for example polymethyl methacrylate.

Apart from the contact with the tray 3, there is no contact whatsoever with the egg 2. The measurement is completely contactless. Light source 4, light tube 9 and light sensors 7 make no contact with the egg 2.

The end of the light tube 9 is located approximately 1 cm from the end of the egg 2.

The vertical arrows 12 show the direction of a force with which the device 1 is made vibration free during the measurement. There is a downward force 12 on the casing (sensor array) 14 and an upward force 12 at the bottom of the tray 3, preferably on the steel plate 18 on which the tray 3 is attached and which delimits the bottom of the device.

The force suppresses external vibrations and also results in a vibration shortcut. If there are still vibrations, light sources, light sensors and eggs will vibrate with the same vibration and/or frequency.

Figure 2:
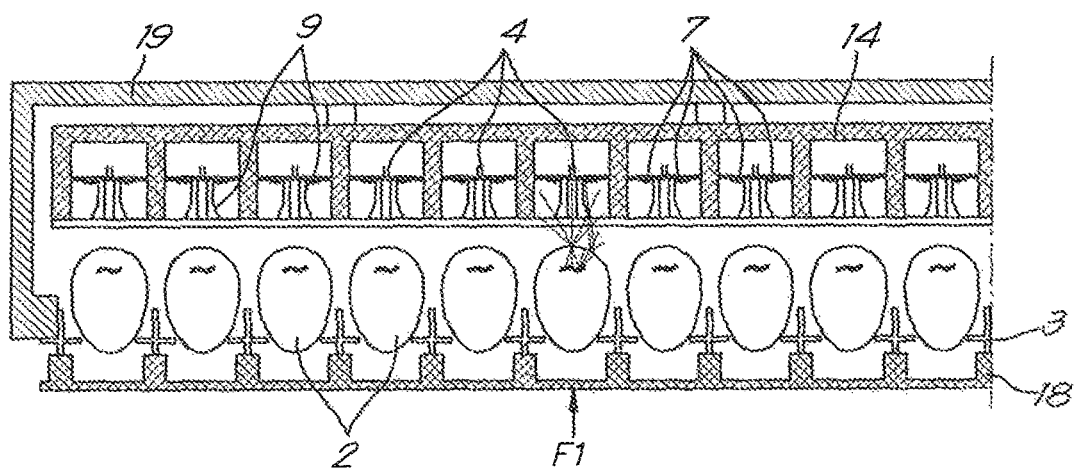
FIG. 2 shows a preferred embodiment of a device according to the invention whereby a tray of several eggs is scanned.

FIG. 2 shows a set-up that comprises several devices 1 according to FIG. 1. For example, a tray can contain 150 eggs in a matrix/array. Above every egg a device 1 is provided with its own light source 4, light tube 9 and light sensors 7. FIG. 2 shows one row of the matrix/array. Light source 4, light tube 9 and light sensors 7 are therefore also provided in a matrix/array (not shown in the figure).

Figure 3:
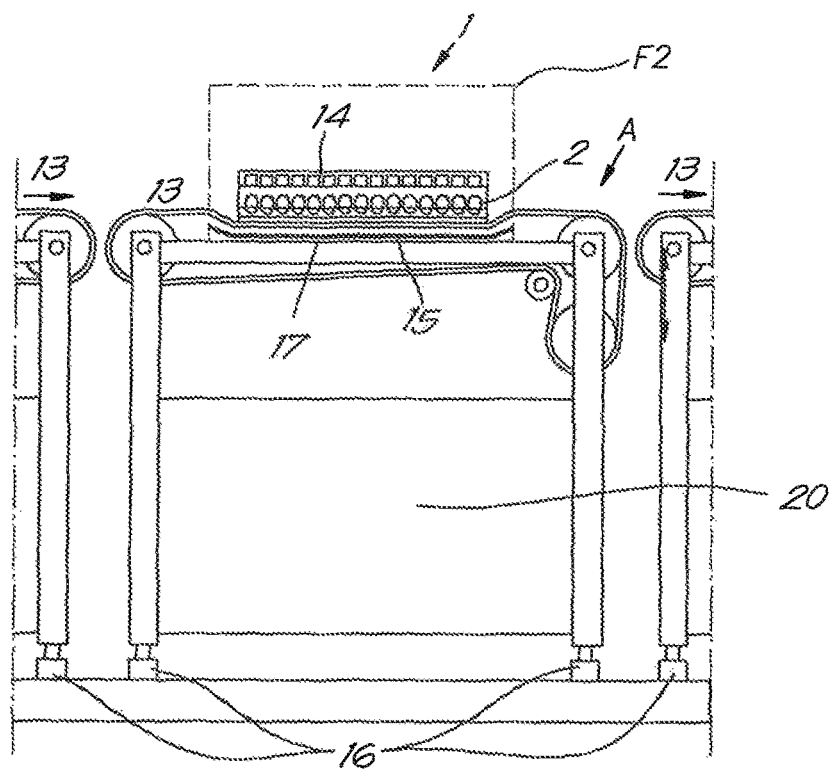
FIG. 3 shows a preferred embodiment of a vibration free set-up of a device 1 according to the invention.

FIG. 3 shows a lateral view of a vibration free set-up of a device 1 according to the invention. Preferably, the eggs 2 are in a grid of x by y eggs. The tray 3 with eggs 2 is supplied via a conveyor belt 13 and placed under the array 14 with light sources 4 and light sensors 7. The array 14 contains one light source 4 per egg and several light sensors 7 per egg.

Preferably, the array 14 can be lifted up to position the incubation tray, tray, or other support 3 with eggs 2. The array 14 is completely loose and free of the eggs, such that no contact is made with the eggs at any time.

During the measurement the set-up is made vibration free to exclude mechanical vibration between the array 14 and the eggs 2. Vibrations are very disadvantageous for the precise measurement of an embryo's heart rate in an egg. Indeed, the signal of the heart rate is very weak compared to possible interference by vibrations.

Preferably, in a vibration free set-up the array 14 with light sources 4 and light sensors 7, the tray 3 with eggs 2 and possibly the conveyor belt 13, at least during the measurement, are kept in place by an appropriate construction. A plate 15 has been provided under the conveyor belt 13 to support the tray 3 when it is pressed against the plate 15, and to make it vibration free. The entire unit is supported on dampers 16. An extra plate 17 is provided to support the conveyor belt 13 and the tray 3. The construction can be provided with a heavy block 20 at the bottom, for example concrete. Consequently, a very rigid and vibration free construction is created, at least during the measurement.

Figure 4:
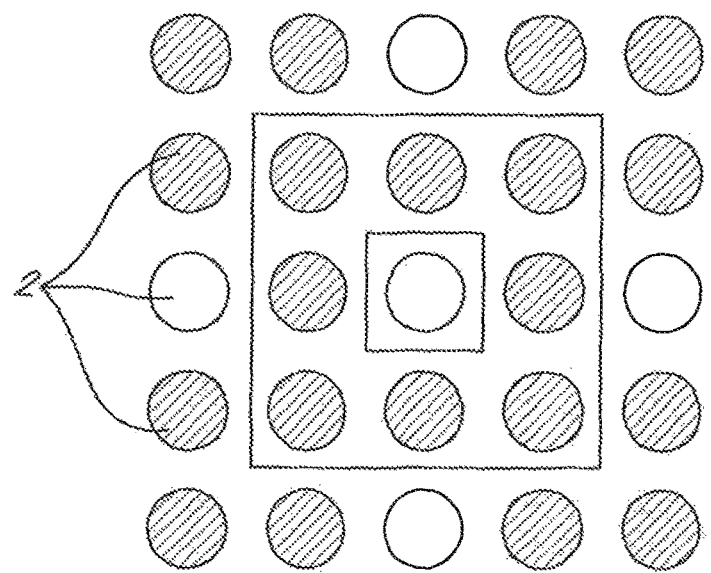
FIG. 4 shows an example of a matrix of 5 by 5 eggs that are scanned.

FIG. 4 shows a scan of an array of 5 by 5 eggs. The shaded eggs cannot be scanned simultaneously with the non-shaded eggs, in other words, neighbouring eggs are not scanned simultaneously. Around every egg that is scanned at a particular moment in time, there is a barrier of non-scanned eggs (shaded). In this way, every egg 2 in the tray is surrounded by 8 eggs (see frame) that will not be scanned at the same moment that the egg in question is scanned. The shaded eggs then serve as shielding or barrier for the light that measures the non-shaded egg. The other eggs 2 (not shaded) can be scanned in the same time slot.

The eggs are scanned in matrix patterns of n by n eggs. This means every egg that is scanned at a certain time is surrounded by $n^2-1$ eggs. In the example of a scan matrix of 3 by 3, 1 egg is therefore surrounded by 8 eggs.

In a scan matrix of 3 by 3 for example, the time is divided into 9 time slots. In time slot 1, egg 1 is measured for example, in time slot 2 egg 2, and in time slot 3 egg 3, etc. Whereby egg 1 does not necessarily have to lie next to egg 2 and egg 2 does not necessarily have to lie next to egg 3.

Such method of scanning avoids interference with the heart rate of embryos of neighbouring eggs during the measurement.

Figure 5:
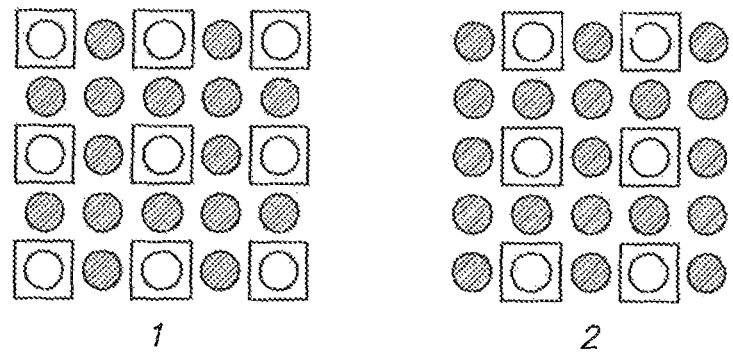
FIG. 5 shows a method for the simultaneous scanning/sampling of eggs.
Figure 5:
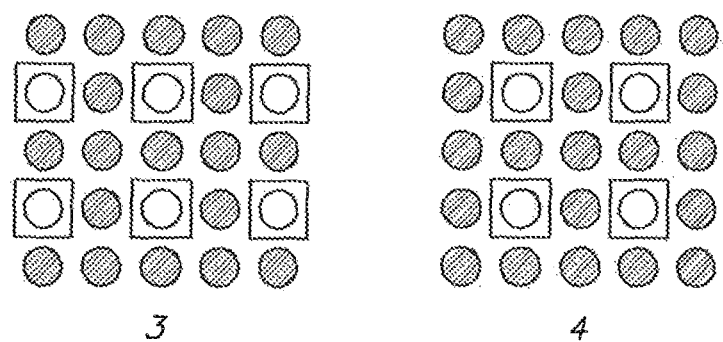

FIG. 5 shows a method for the simultaneous scanning of eggs. During scan 1 the eggs with number 1 are scanned, during scan 2 the eggs with number 2, during scan 3 the eggs with number 3, and during scan 4 the eggs with number 4. In this way an optimum number of non-neighbouring eggs are scanned at the same time.

The scan speed is sufficiently high such that a quick measurement is obtained, even if not all the eggs of the tray are measured at the same time.

Figure 6:
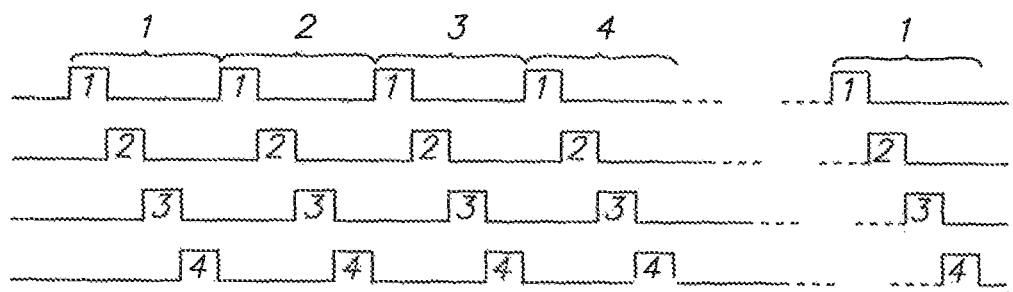
FIG. 6 shows a time schedule for the scanning/sampling.

FIG. 6 shows a time schedule for the scan. The eggs numbered 1, 2, 3 and 4 are scanned after each other in a subsequent time frame or time slot. This is repeated n times, e.g. 256 times. Thus, every egg is measured n times in a different time slot. The total measurement time for a tray of eggs is about 2.5 seconds and about 256 measurements per egg. For a tray of 150 eggs, the total amount of measurements per tray is 256×150=38.400.

During the measuring the tray is kept under a pressure force to prevent that the eggs vibrate.

The n signals of every egg are processed into a signal that varies in time that is representative for an embryo's heart rate in the egg in question.

Unlike other systems the measurement is not continuous.

Every time a scan or sample is taken of a particular egg, or a certain position, the light source is switched on and off and practically synchronously or simultaneously with this the light sensors too. The necessary electronics means and algorithms are applied for this.

The present invention is by no means limited to the embodiments described as an example and shown in the drawings, but a device to measure the heart rate of an embryo in an egg according to the invention as defined by the claims can be realised in all kinds of variants without departing from the scope of the invention.

The invention claimed is:

1. Device for measuring of an embryo's heart rate in an egg whereby infrared light is sent in the egg by a light source, and the reflection of that light is detected by one or more light sensors and converted into a signal that is representative for the heart rate,
   wherein the device comprises the light source whereby a light tube is provided between the light source and the egg, wherein the light tube is internally dimensioned and positioned such that a focused light spot is directed on the egg, and the light tube is dimensioned and positioned such that light reflected on the surface of the egg on the level of the light spot cannot directly reach the light sensors;

wherein a length of a light tube is such that the light is directed on the egg in a fine beam;

wherein on one end the light tube is provided around the light source so no light can escape, and on the other end the light tube comes close to the egg without making contact with the egg;

wherein the light tube is provided with a widened edge at least at the end of the light tube near the egg; and wherein the one or more light sensors are provided around the light source and the light sensors are located in the shadow field of the widened edge of the light tube.

2. Device (1) according to claim 1, wherein the light source (4) can be wholly or partly contained in the light tube (9).

3. Device (1) according to claim 1, wherein the half exit angle of the light source (4) is 3° to 4°.

4. Device (1) according to claim 1, wherein the light tube (9) can be provided with means that bundles the light in a fine beam.

5. Device (1) according to claim 1, wherein the light tube (9) is cylindrical both on the inside and the outside.

6. Device (1) according to claim 1, wherein the light sensors (7) are provided around and in the same plane as the light source (4).

7. Device (1) according to claim 1, wherein the light sensors (7) are located around the light source in a curved surface.

8. Device (1) according to claim 1, wherein three or six light sensors (7) are used.

9. Device (1) according to claim 1, wherein the broadened edge is dimensioned and positioned such that light from the light spot reflected on the surface of the egg cannot directly reach the light sensors.

10. Device (1) according to claim 1, wherein the device (1) comprises means to suppress mechanical vibrations on the light source (4), the light sensors (7) and the eggs (2).

11. Device (1) according to claim 1, comprising measuring means, whereby a tray (3) is provided to hold a matrix of eggs (2) and above the eggs a sensor array (14) is provided per egg comprising a light source (4), light tube (9) and light sensors (7), wherein at least during the measurement, a mechanical shortcut is provided between the tray (3) and the sensor array (14), or between the tray (3) and the measurement means, so as to eliminate vibrations or to vibrate with the same frequency.

12. Device (1) according to claim 1, wherein the mechanical shortcut comprises un upward and/or downward pressure force.

13. Device (1) according to claim 1, wherein the light source (4) consists of an IR LED or a laser beam.

14. Device (1) according to claim 1, wherein the infrared light source (4) emits light with a wavelength in the range between 700 nm and 1100 nm.

15. Device (1) according to claim 1, wherein the device (1) comprises means which keep the luminous intensity of the light source (4) stable.

16. Device (1) according to claim 1, wherein the light sensor (7) is sensitive to the wavelength of the emitted IR light of the light source (4).

17. Device (1) according to claim 1, wherein the device (1) is able to detect very low frequencies, from 0.5 Hz to 7 Hz for a heart rate from 30 to 420 beats per minute.

18. Device (1) according to claim 1, wherein only one focused light source is used.

19. Device (1) according to claim 1, wherein the device is provided with a matrix of eggs (2) whereby the eggs (2) are each provided with their own light source (4), light tube (9) and one or more light sensors (7).

20. Device (1) according to claim 1, wherein both the heart rate and the embryo's movement are measured.

21. Device (1) according to claim 1, wherein the device is provided with means to determine the sample sequence whereby every egg (2) is sampled several times with an interval and per egg (2) a signal is formed with the multiple samples of the egg in question, whereby the variation of the signal shows the viability of an egg.

22. Device (1) according to claim 21, wherein neighbouring eggs (2) are not sampled at the same time.

23. Method for measuring an embryo's heart rate in an egg, by means of a device (1) according to claim 1, comprising the following steps:
   a. Determining a sample sequence for the simultaneous measuring of non-neighbouring eggs,
   b. Simultaneously sampling of the eggs of a sample sequence, and subsequently repeating for the eggs of another sequence,
   c. Repeating step b n times,
   d. Processing the n signals per egg into a signal varying in time representative for the embryo's heart rate or viability in the egg.

24. Method according to claim 23, whereby in step a sample sequence 1 comprises first selected non-neighbouring eggs in a matrix, sample sequence 2 comprises second selected non-neighbouring eggs in the matrix, sample sequence 3 comprises third selected non-neighbouring eggs in the matrix, and sample sequence 4 comprises fourth selected non-neighbouring eggs in the matrix, and whereby in step b the selected eggs of sample sequence 1, 2, 3 and 4 are scanned in a consecutive time slot.

25. Method according to claim 23, whereby per measurement of the eggs in step b the light source (4) and light sensors (7) of the selected eggs are synchronously switched on and off.

26. Method according to claim 23, whereby the total measurement time for a tray (3) of 150 eggs is 2.5 seconds.

27. Method according to claim 23, whereby there are 256 measurements per egg.

28. Method according to claim 23, whereby during the measurement the light source (4) and light sensors (7), and the eggs (2) are positioned vibrationless.

29. Method according to claim 23, whereby the measurements are not continuous.

30. Method according to claim 23, whereby the measurements are contactless.

31. Method according to claim 23, whereby only one focused light source is used.

* * * * *